(12) United States Patent
Chung et al.

(10) Patent No.: US 7,939,495 B2
(45) Date of Patent: May 10, 2011

(54) METHOD FOR IMPROVING SKIN CONDITIONS

(75) Inventors: Yong Ji Chung, Gyeonggi-do (KR); Young Deug Kim, Gyeonggi-do (KR); Chung Ryul Kim, Gyeonggi-do (KR)

(73) Assignee: Caregen Co., Ltd, Gunpo-si, Gyeonggi-do (KR)

( * ) Notice: Subject to any disclaimer, the term of this patent is extended or adjusted under 35 U.S.C. 154(b) by 141 days.

(21) Appl. No.: 12/083,970

(22) PCT Filed: Oct. 24, 2006

(86) PCT No.: PCT/KR2006/004350
§ 371 (c)(1), (2), (4) Date: Jun. 26, 2008

(87) PCT Pub. No.: WO2007/049904
PCT Pub. Date: May 3, 2007

(65) Prior Publication Data
US 2009/0124556 A1     May 14, 2009

(30) Foreign Application Priority Data
Oct. 24, 2005 (KR) .................. 10-2005-0100391

(51) Int. Cl.
*A61K 38/18* (2006.01)
*C07K 14/50* (2006.01)

(52) U.S. Cl. .................. 514/9.1; 514/21.6
(58) Field of Classification Search .................. None
See application file for complete search history.

(56) References Cited

U.S. PATENT DOCUMENTS

| | | | |
|---|---|---|---|
| 5,143,829 A | | 9/1992 | Thompson et al. |
| 6,010,999 A | * | 1/2000 | Daley et al. ............ 514/2 |
| 6,046,164 A | * | 4/2000 | Asano et al. ............ 514/12 |
| 6,294,359 B1 | * | 9/2001 | Fiddes et al. ............ 435/69.4 |
| 6,548,634 B1 | | 4/2003 | Ballinger et al. |
| 2002/0119931 A1 | | 8/2002 | Facchiano et al. |

OTHER PUBLICATIONS

Uhl, E., et al., "Improvement of Skin Flap Perfusion by Subdermal Injection of Recombinant Human Basic Fibroblast Growth Factor", *Ann Plast Surg*, vol. 32, pp. 361-366, (1994).

* cited by examiner

*Primary Examiner* — Christine J Saoud
(74) *Attorney, Agent, or Firm* — The Nath Law Group; Joshua B. Goldberg; Mihsuhn Koh (57) ABSTRACT

Provided is a method for improving a skin condition or treating a periodontal disease, which includes administering to a subject a composition including a basic fibroblast growth factor-derived peptide as an active ingredient. The present method effectively improves skin conditions and treats periodontal diseases. In addition, the present peptides can be applied to pharmaceutical compositions, cosmetics, toothpaste and compositions for mouth cleaning and care.

7 Claims, 8 Drawing Sheets

```
                        SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: peptide having functions and actions of basic
      fibroblast growth factor

<400> SEQUENCE: 1

Tyr Arg Ser Arg Lys Tyr Thr Ser Trp Tyr
1               5                   10
```

METHOD FOR IMPROVING SKIN CONDITIONS

This is a National Phase Application filed under 35 U.S.C. 371 of International Application No. PCT/KR2006/004350, filed Oct. 24, 2006, claiming benefit of Korean Application No. 10-2005-0100391 filed on Oct. 24, 2005.

BACKGROUND OF THE INVENTION

1. Field of the Invention

The present invention relates to a composition for improving a skin condition or treating a periodontal disease, which comprises as an active ingredient a basic fibroblast growth factor-derived peptide.

2. Description of the Related Art

Fibroblast growth factor plays a role as a mitogenic factor in fibroblasts and epithelial cells. Bovine brain or pituitary gland-derived fibroblast growth factor (FGF) was first suggested by Gospodarowicz in the year of 1974 (*Nature* 249: 123-127 (1974)). Subsequently, it was reported that the mitogenic factor isolated from the brain is different from that isolated from the pituitary gland. Although these two factors show similar biological activities, they are different from each other in terms of amino acid sequences and isoelectric points, named as acidic FGF and basic FGF, respectively. Both of acidic FGF (aFGF) and basic FGF (bFGF) are classified into heparin binding growth factors affecting to proliferation potential of mesoderm- and neuroectoderm-originated cells such as endothelial cells, smooth muscle cells, adrenal cortex cells, prostatic and retinal epithelium, neuroglial cells, astrocytes, chondrocytes, stem cells and osteoblasts (Burgess and Maciag, *Ann. Rev. Biochem.* 58:584 (1989)).

FGF induces mitogenic reactions to stimulate cell proliferation and stimulates almost all cell types to trigger responses in a non-mitogenic manner as well. These activities of FGF are responsible for promoting cell migration to a wound site (chemotaxis), triggering the formation of new blood vessels (angiogenesis), controlling nerve regeneration (neurotrophic), expression of certain proteins in cells, the formation of extracellular matrix and stimulation or inhibition of the viability of cells involved in wound healing (Burgess, W. H., and Maciag, T. *Ann. Rev. Biochem.* 58:584-588 (1989)). Together with promoting cell proliferation, these responses described above provide grounds and principles underlying actions of fibroblast growth factor on wound healing and treatment of thrombosis and arteriosclerosis. Therefore, FGF has been suggested to promote wound healing (Davidson, J. M., et al. *J. Cell Bio.* 100:1219-1227 (1985)), to reduce damages of myocardium associated with surgical operations or heart diseases (U.S. Pat. No. 4,378,347), and to increase survival of neurons and the extension of axons (Walicke, P., et al. *Proc. Nat. Acad. Sci. USA* 83:3012-3016 (1986)).

bFGF having a molecular weight of about 18 kDa is a basic protein (pI 9.58) secreted mainly in pituitary glands and has been reported to enhance growth of various mesoderm-derived cells. Also, it has been proposed that bFGF enhancing growth of vascular endothelial cells and smooth muscle cells shows excellent efficacies in wound healing, angiogenesis, skin elasticity by increasing biosynthesis of collagen and elastin and growth of normal cells (Pilcher B K., et al. *J. Biol. Chem.* 272(29):18147-18154 (1997)). In addition, bFGF has been reported to activate circulation and hair root cells in scalp (Kristen L. Mueller. et al. *J. Neurosci.* 22(2):9368-9377 (2002)).

However, polypeptide growth factors present in blood and tissues have in vivo half life as short as several minutes. In particular, since bFGF has four cysteine residues not involved in the formation of disulfide bonds, it shows very poor stability.

In addition, since bFGF is biologically unstable and physiochemically heterogeneous, it is likely to show reduced treatment efficacies. Its skin permeation is far poor.

Accordingly, there remain needs to improve stability and skin permeation of bFGF so as to increase applicability of bFGF to a variety of formulations.

DETAILED DESCRIPTION OF THIS INVENTION

For developing novel peptides for improving skin conditions and treating periodontal diseases, the present inventors have made intensive researches to prepare and screen a variety of human bFGF-originated peptides. As a result, the present inventors have discovered a novel peptide having superior efficacies as well as improved stability, eventually accomplishing the present invention.

Accordingly, it is an object of this invention to provide a composition for improving a skin condition or treating a periodontal disease.

It is another object of this invention to provide a method for improving a skin condition or treating a periodontal disease.

It is still another object of this invention to provide a use of a bFGF-derived peptide for manufacturing a composition for improving a skin condition or treating a periodontal disease.

It is further object of this invention to provide a modified bFGF-derived peptide having improved stability.

Other objects and advantages of the present invention will become apparent from the following detailed description together with the appended claims and drawings.

In one aspect of this invention, there is provided a composition for improving a skin condition or treating a periodontal disease, which comprises as an active ingredient a peptide comprising the amino acid sequence of SEQ ID NO: 1.

In another aspect of this invention, there is provided a method for improving a skin condition or treating a periodontal disease, which comprises administering to a subject a composition comprising a peptide comprising the amino acid sequence of SEQ ID NO:1 as an active ingredient.

In still another aspect of this invention, there is provided a use of a peptide comprising the amino acid sequence of SEQ ID NO:1 as an active ingredient for manufacturing a composition for improving a skin condition or treating a periodontal disease.

For developing novel peptides for improving skin conditions and treating periodontal diseases, the present inventors have made intensive researches to prepare and screen a variety of human bFGF-originated peptides. As a result, the present inventors have discovered a novel peptide having superior efficacies as well as improved stability. Furthermore, the present inventors have prepared modified-peptides by modifying the amino acid sequence of human bFGF-originated peptides having much better stability to physiochemical factors such as heat, acid and alkali.

The peptide used as active ingredients in the composition of this invention comprises the bFGF-derived amino acid sequence of SEQ ID NO:1. Preferably, the peptide consists essentially of the amino acid sequence of SEQ ID NO:1. Most Preferably, the peptide consists of the amino acid sequence of SEQ ID NO:1.

The term used herein "peptide" refers to a linear molecule formed by linking amino acid residues through peptide bonds.

The peptides of the invention may be prepared by conventional chemical synthesis processes known to one of skill in the art, in particular, solid-phase synthesis techniques (Merrifield, *J. Amer. Chem. Soc.* 85:2149-54(1963); Stewart, et al., *Solid Phase Peptide Synthesis*, 2nd. ed., Pierce Chem. Co.: Rockford, 111(1984)).

bFGF-derived peptides having suggested so far have been provided as antagonists to bFGF (e.g., U.S. Pat. No. 7,009, 036). In contrast, the peptides of this invention show in vivo functions and efficacies identical or similar to natural-occurring bFGF. In other words, although known bFGF-derived peptides exert anti-bFGF activities in vivo, the peptide of this invention shows bFGF activities by mimicking the actions of natural-occurring bFGF. In this regard, the peptide of this invention is distinctly different from the known other peptides.

The composition of this invention has efficacies and activities to improve skin conditions. In particular, the peptides used as active ingredients in the present composition show excellent skin permeation because of their low molecular weight. Accordingly, where the present composition is topically applied to skin, it becomes evident that skin conditions are considerably improved. More still preferably, the improvement in the skin condition by the present composition includes the improvement in wrinkle or skin elasticity, the prevention of skin aging, the prevention of hair loss, the promotion of hair growth, the improvement in skin moisture, the removal of dark spots and the treatment of acne, most preferably, the improvement in wrinkle or skin elasticity, and the prevention of skin aging.

For example, the peptides used as active ingredients in the present composition promote the proliferation of fibroblasts or keratinocytes, induce the biosynthesis of procollagen, laminin, hyaluronic acid and fibronectin to regenerate keratinocyte layer, epidermis and dermis, thereby resulting in the improvements in wrinkle, skin elasticity and skin moisture, and the prevention of skin aging.

In addition, the peptides used as active ingredients in the present composition activate the circulation and hair root cells in scalp and maintain anagen phase in hair growth cycle, as natural-occurring bFGF (Kristen L. Mueller. et al. *J. Neurosci.* 22(2):9368-9377(2002)), showing the prevention of hair loss or the promotion of hair growth.

According to a preferred embodiment, the composition of this invention has the treatment efficacy on the periodontal disease and is toothpaste or a composition for tooth and mouth cleaning or caring. The term "composition for treating periodontal diseases" may be interchangeably used herein with other terms, "composition for tooth and mouth caring" and "composition for tooth and mouth cleaning".

The peptide of this invention promotes biological activities of fibroblasts present in gum tissues and heals gum wound to regenerate damaged gum tissues, thereby treating or preventing periodontal diseases.

Even though the peptide of this invention per se has higher stability than natural-occurring bFGF, its modification enables to have much higher stability. Preferably, the amino acid sequence of SEQ ID NO:1 has at least one amino acid residue protected with acetyl group, fluorenyl methoxy carbonyl group, formyl group, palmitoyl group, myristyl group, stearyl group or polyethylene glycol, most preferably, acetyl group.

The term used herein "stability" refers to in vivo stability and storage stability (e.g., storage stability at room temperature) as well. The protection group described above protects the peptides from the attack of protease in vivo.

More preferably, the amino acid residue protected with the protection group is Tyr residue at the N- or C-terminal, most preferably, N-terminal of the amino acid sequence of SEQ ID NO:1. Preferably, —COOH group of the Tyr residue at the C-terminal of the amino acid sequence of SEQ ID NO:1 is modified to —OH or —NH$_2$ to enhance the stability of peptides.

Since the present peptides, preferably, modified peptides having protection groups are protected at their N- and/or C-terminal, their thermal stability at 37° C. is enhanced and their stability to physiochemical factors such as acid and alkali is also excellent. Therefore, since the peptides of this invention have significant long-term storage stability, they can be advantageously applied to products requiring long-term storage such as drugs, quasi-drugs, cosmetics and tooth/mouth cleaning or caring products.

The present composition may be prepared as a pharmaceutical or cosmetic composition.

According to a preferred embodiment, the composition is a pharmaceutical composition comprising (a) a pharmaceutically effective amount of the peptide comprising the amino acid sequence of SEQ ID NO:1; and (b) a pharmaceutically acceptable carrier.

The term used herein "pharmaceutically effective amount" refers to an amount enough to show and accomplish efficacies and activities of the peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, administered parenterally, e.g., by intravenous, intraperitoneal, intramuscular, subcutaneous, transdermal or local administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.0001-100 µg.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferred embodiment, the composition is a cosmetic composition comprising (a) a cosmetically effective amount of the peptide comprising the amino acid sequence of SEQ ID NO:1; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softener, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents, for example ethoxylated isostearyl alcohols, polyoxyethylene sorbitol esters and poly oxyethylene sorbitan esters, miocrystalline cellulose, aluminum metahydroxide, bentonite, agar and tragacanth or mixtures of these substances.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as peptides as active ingredients and carriers. The non-limiting examples of auxiliaries include preservatives, antioxidants, stabilizers, solubilizers, vitamins, colorants, odor improvers or mixtures of these substances.

In further aspect of this invention, there is provided a peptide having higher stability than naturally occurring basic fibroblast growth factor, wherein the peptide comprises the amino acid sequence of SEQ ID NO:1 and the amino acid sequence of SEQ ID NO:1 has at least one amino acid residue protected with a protection group selected from the group consisting of acetyl group, fluorenyl methoxy carbonyl group, formyl group, palmitoyl group, myristyl group, stearyl group or polyethylene glycol (PEG).

Since the protected-peptide of this invention is used as active ingredients in the present composition, the common descriptions between them are omitted in order to avoid undue redundancy leading to the complexity of this specification.

The peptide used as active ingredients in the present invention has identical or similar functions or actions to human bFGF and its biological activity is almost identical to natural-occurring bFGF. In addition, the peptide of this invention exhibits much higher stability and skin permeation than natural-occurring bFGF. In these connections, the composition comprising the peptides of this invention can exhibit excellent efficacies on improvement in skin conditions and treatment of periodontal diseases. In addition, the peptide of this invention can be advantageously applied to drugs, cosmetics, toothpaste and compositions for mouth cleaning and caring.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Synthesis of Fmoc-Tyr(tBu)-Arg(pbf)-Ser(tBu)-Arg (pbf)-Lys(Boc)-Tyr(tBu)-Thr(tBu)-Ser(tBu)-Trp (Boc)-Tyr(tBu)-Rink Amide Resin 1.42 g (1 mmole) of Fmoc-Rink amide resin (Nova Biochem Cat No. 01-64-0013) was introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of a deprotection solution (20% piperidine/DMF) were added to the reactor and agitation for 10 min at room temperature and solution removal were performed. After adding the same volume of the deprotection solution, the reaction was undertaken for 10 min and solution was removed, followed by washing sequentially with DMF, MC and DMF. 10 ml of DMF solution was added to a new reactor and then 2 mmole of Fmoc-Tyr(tbu)-OH (Nava Biochem, USA), 2 mmole of HoBt and 2 mmole of Bop were added, followed by agitation for solubilization. 4 mmole of DIEA (N,N'-Diisopropyl ethylamine) was added to the reactor and agitation was carried out to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution to remove unreacted residuals. The reacted resin was taken to evaluate extent of reactions by Ninhydrine test. Using the deprotection solution, the deprotection was performed twice in the same manner as described above to yield Tyr(tbu)-Rink amide resin. After washing with DMF and MC, Ninhydrine test was carried out and the attachments of amino acids were performed as described above. Based on the amino acid sequence designed by the present inventors, Fmoc-Trp(Boc), Fmoc-Ser(tBu), Fmoc-Thr(tBu), Fmoc-Tyr(tBu), Fmoc-Lys(Boc), Fmoc-Arg (pbf), Fmoc-Ser(tBu), Fmoc-Arg(pbf) and Fmoc-Tyr(tBu) were attached to resins. The prepared peptidyl resin was washed three times with DMF, MC and methanol, respectively and dried under nitrogen atmosphere, after which it was vacuum-dried under $P_2O_5$, finally giving Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-Rink amide resin.

Example 2

Synthesis of Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-CTL-resin 700 mg of chloro trityl chloride resin (CTL resin, Nova Biochem Cat No. 01-64-0021) were introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Tyr(tBu)-OH and 400 mmole of DIEA were then added to the reactor, after which the mixture was dissolved by agitation and reaction was then undertaken with agitating for 1 hr. After washing, methanol and DIEA (2:1) dissolved in MC were reacted with the resin for 10 min, and then the resultant was washed using excess of DCM/DMF (1:1). After removing the solution, 10 ml of DMF were added to the resultant and agitation was performed for 3 min, followed by removing the solvent. 10 ml of a deprotection solution (20% piperidine/DMF) were added to the reactor and agitation for 10 min at room temperature and solution removal were performed. After adding the same volume of the deprotection solution, the reaction was undertaken for 10 min and solution was removed, followed by washing sequentially with DMF, MC and DMF to yield Tyr-(tBu)-CTL resins. 10 ml of DMF solution was added to a new reactor and then 200 mmole of Fmoc-Trp(Boc)-OH(Novabiochem, USA), 200 mmole of HoBt and 200 mmole of Bop were added, followed by agitation for solubilization. 400 mmole of DIEA (N,N'-Diisopropyl ethylamine) was added to the reactor and agitation was carried out to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution to remove unreacted residuals. The reacted resin was taken to evaluate extent of reactions by Ninhydrine test. Using the deprotection solution, the deprotection was performed twice in the same manner as described above to yield Trp(Boc)-Tyr(tBu)-CTL resin. After washing with DMF and MC, Ninhydrine test was carried out and the attachments of amino acids were performed as described above. Based on the amino acid sequence designed by the present inventors, Fmoc-Ser(tBu), Fmoc-Thr(tBu), Fmoc-Tyr(tBu), Fmoc-Lys(Boc), Fmoc-Arg(pbf), Fmoc-Ser(tBu), Fmoc-Arg(pbf) and Fmoc-Tyr(tBu) were attached to resins. The prepared peptidyl resin was washed three times with DMF, MC and methanol, respectively and dried under nitrogen atmosphere, after which it was vacuum-dried under $P_2O_5$, finally giving Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-CTL resin.

Example 3

Synthesis of Fmoc-Decapeptide (Fmoc-YRSRKYTSWY-$NH_2$)

Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-Rink amide resin prepared in Example 1 was reacted with 30 ml of a leaving solution [containing 81.5% trifluoroacetic acid (TFA), 5% distilled water, 5% thioanisole, 5% phenol, 2.5% EDT and 1% TIS] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.18 g of unpurified Fmoc-decapeptide (Fmoc-YRSRKYTSWY-$NH_2$) (yield 70.6%). The molecular weight of the final product was measured as 1631.5 (theoretical MW 1630.84) using a molecular weight analyzer (Perseptive Pioneer DE-STR ABI, USA).

Example 4

Synthesis and Purification of Ac-Decapeptide (Ac-YRSRKYTSWY-$NH_2$)

Figure 1:
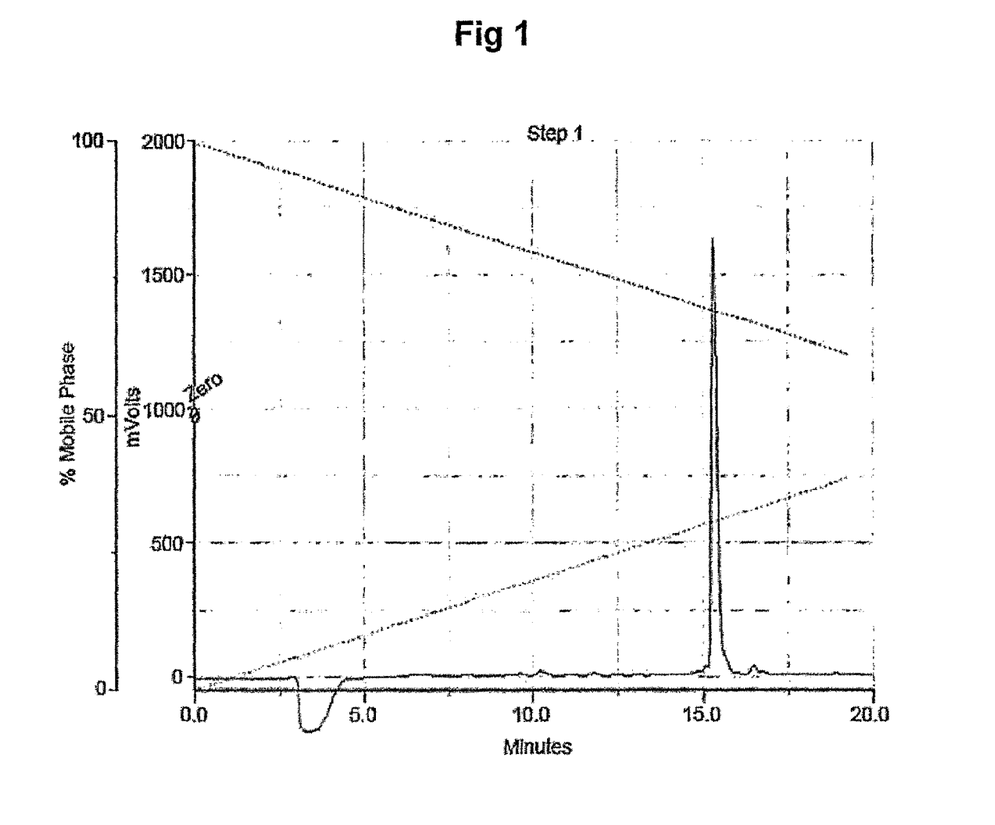
FIG. 1 represents results of high performance liquid chromatography analysis of the acetyl-decapeptide prepared in Example.
Figure 2:
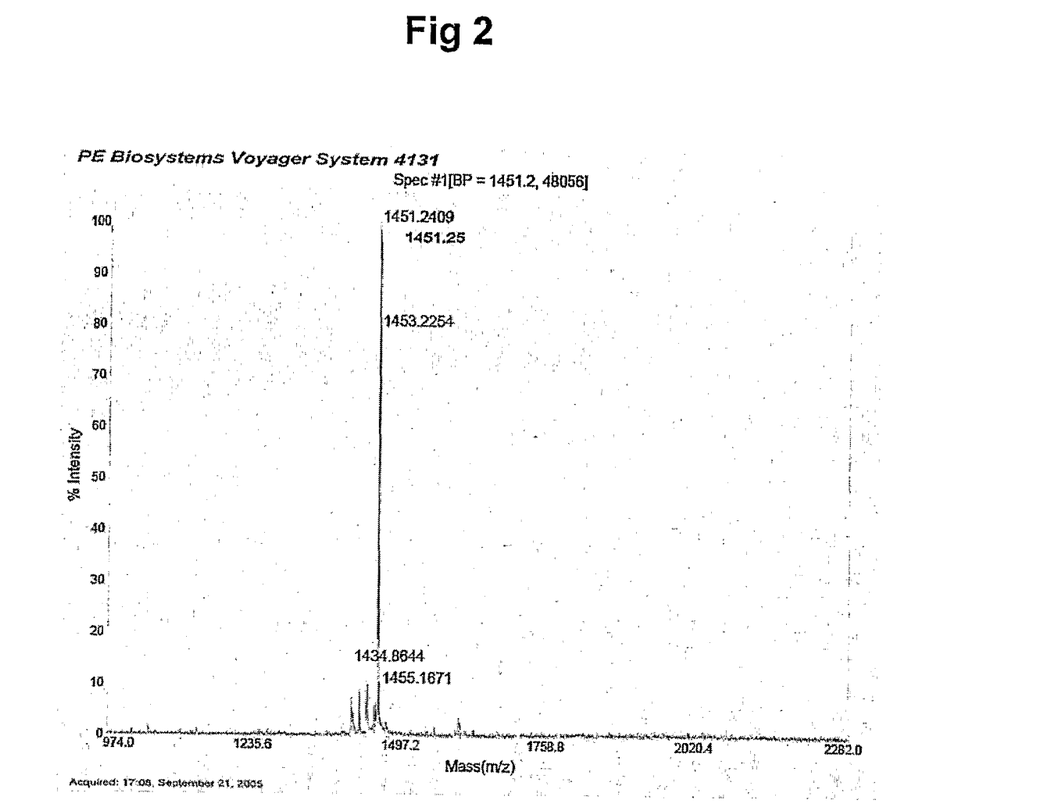
FIG. 2 represents results of mass spectroscopy analysis of the acetyl-decapeptide prepared in Example.

Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-Rink amide resin prepared in Example 1 was reacted twice with the deprotection solution for 10 min to remove Fmoc-protecting group. 2 ml of acetic acid anhydride, 2 mmole HoBt and 2 mmole Bop were introduced into a new reactor, and then 4 mmole DIEA was added to the reactor, followed by agitating. Premade acetic acid anhydride was introduced into the reactor containing the resin and the reaction was undertaken for 30 min. The resin was washed three times sequentially with DMF, MC and methanol and completely dried. The dried peptidyl resin was added to a round bottom flask and reacted with 30 ml of the leaving solution [containing 81.5% TFA, 5% distilled water, 5% thioanisole, 5% phenol, 2.5% EDT and 1% TIS] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 0.93 g of unpurified acetyl-decapeptide (Ac-YRSRKYTSWY-NH$_2$) (yield 62.3%). The unpurified peptides were fractionated using a high performance liquid chromatography, and major peptides were collected and subjected to distillation to remove acetonitrile, followed by lyophilization to give purified peptides of interest. The finally prepared peptide was analyzed using high performance liquid chromatography to show 92% purity (FIG. 1). The final yield was 48%. The molecular weight of the final product was measured as 1451.3 (theoretical MW 1450.63) using a mass analyzer, demonstrating that the peptide of interest, Ac-YRSRKYTSWY-NH$_2$ was successfully synthesized (FIG. 2).

Example 5

Synthesis of Formyl-Decapeptide (Formyl-YRSRKYTSWY-NH$_2$)

Fmoc-Tyr(tBu)-Arg(pbf)-Ser(tBu)-Arg(pbf)-Lys(Boc)-Tyr(tBu)-Thr(tBu)-Ser (tBu)-Trp(Boc)-Tyr(tBu)-Rink amide resin prepared in Example 1 was reacted twice with the deprotection solution for 10 min to remove Fmoc-protecting group. 2 mmole formic acid, 2 mmole HoBt and 2 mmole Bop were introduced into a new reactor, and then 4 mmole DIEA was added to the reactor, followed by agitating. Pre-made acetic acid anhydride was introduced into the reactor containing the resin and the reaction was undertaken for 30 min. The resin was washed three times sequentially with DMF, MC and methanol and completely dried. The dried peptidyl resin was added to a round bottom flask and reacted with 30 ml of the leaving solution (containing 81.5% TFA, 5% distilled water, 5% thioanisole, 5% phenol, 2.50% EDT and 1% TIS) for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.03 g of unpurified formyl-decapeptide (Formyl-YRSRKYTSWY-NH$_2$) (yield 69.7%). The molecular weight of the final product was measured as 1437.3 (theoretical MW 1436.6) using a molecular weight analyzer.

Example 6

Synthesis of Palmitoyl-Decapeptide (Palmitoyl-YRSRKYTSWY-NH$_2$)

Fmoc-Tyr(tBu)-Arg(pbf)-Ser(tBu)-Arg(pbf)-Lys(Boc)-Tyr(tBu)-Thr(tBu)-Ser (tBu)-Trp(Boc)-Tyr(tBu)-Rink amide resin prepared in Example 1 was reacted twice with the deprotection solution for 10 min to remove Fmoc-protecting group. 1.5 mmol palmitoyl chloride (Sigma-Aldrich) in 5 ml DMF and 1.56 ml of DIPEA were introduced the reactor containing the resin and reaction was carried out for 1 hr at 35° C. The resultant was washed three times with 30 ml DMF and four times with 30 ml DCM and dried under nitrogen atmosphere and then dried using P$_2$O$_5$ under reduced pressure, yielding decapeptides having side chains protected with palmitoyl groups. 1 g of the dried peptidyl resin was added to a round bottom flask and reacted with 10 ml of the leaving solution (containing 81.5% TFA, 5% distilled water, 5% thioanisole, 5% phenol, 2.5% EDT and 1% TIS) for 1 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.25 g of unpurified palmitoyl-decapeptide (palmitoyl-YRSRKYTSWY-NH$_2$) (yield 73.4%). The molecular weight of the final product was measured as 1663.9 (theoretical MW 1663.01) using a molecular weight analyzer.

Examples 7-8

Synthesis of Myristyl-Decapeptide (Myristyl-YRSRKYTSWY-NH$_2$) and Stearyl-Decapeptide (Stearyl-YRSRKYTSWY-NH$_2$)

Fmoc-Tyr(tBu)-Arg(pbf)-Ser(tBu)-Arg(pbf)-Lys(Boc)-Tyr(tBu)-Thr(tBu)-Ser (tBu)-Trp(Boc)-Tyr(tBu)-Rink amide resins synthesized in Example 1 were divided into two batches and reacted twice with the deprotection solution for 10 min to remove Fmoc-protecting group. 1.5 mmol myristyl chloride (Sigma-Aldrich) in 5 ml DMF (myristyl-decapeptide) for or 1.5 mmol stearyl chloride (Sigma-Aldrich) in 5 ml DMF (stearyl-decapeptide) and 1.56 ml of DIPEA were introduced the reactor containing the resin and reaction was carried out for 1 hr at 35° C. The resultant was washed three times with 30 ml DMF and four times with 30 ml DCM and dried under nitrogen atmosphere and then dried using P$_2$O$_5$ under reduced pressure, yielding decapeptides having side chains protected with myristyl or stearyl groups. 1 g of the dried peptidyl resin was added to a round bottom flask and reacted with 10 ml of the leaving solution (containing 81.5% TFA, 5% distilled water, 5% thioanisole, 5% phenol, 2.5% EDT and 1% TIS) for 1 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.26 g of unpurified myristyl-decapeptide (myristyl-YRSRKYTSWY-NH$_2$) (yield 75.2%) and 1.34 g of unpurified stearyl-decapeptide (stearyl-YRSRKYTSWY-NH$_2$) (yield 77.4%).

The molecular weights of the final products were measured as 1634.9 (theoretical MW 1634.96) for myristyl-decapeptide and 1692.2 (theoretical MW 1691.1) for stearyl-decapeptide using a molecular weight analyzer.

Example 9

Synthesis of Fmoc-Decapeptide (Fmoc-YRSRKYTSWY-OH)

Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-CTL-resin prepared in Example 2 was reacted with a solution consisting of TFA, TIS and water (mole ratio of 95:2.5:2.5) for 1 hr and filtered. The resin was washed with a small volume of TFA solution, after which the filtrate was combined with the mother liquor. After distillation under reduced pressure to reduce the total volume by two, the precipitation was induced using excess of cold ether and the formed precipitates were collected by centrifugation, followed by washing twice with cold ether. The resultant was dried under nitrogen atmosphere to give 1.3 g of unpurified Fmoc-decapeptide (Fmoc-YRSRKYTSWY-OH) (yield 77.7%). The molecular weight of the final product was measured as 1632.5 (theoretical MW 1631.84) using a molecular weight analyze.

Example 10

Synthesis of Acetyl-Decapeptide
(Ac-YRSRKYTSWY-OH)

Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-CTL-resin prepared in Example 2 was swelled using DMF, reacted twice with 20% piperidine/DMF solution for 10 min and washed to remove Fmoc protecting groups. 2 ml of acetic acid anhydride, 610 mg of HoBt and 1.77 g of Bop were introduced into a new reactor, and then 1.56 ml of DIEA was added to the reactor, followed by agitating. Pre-made acetic acid anhydride was introduced into the reactor containing the resin and the reaction was undertaken for 30 min. The resin was washed three times sequentially with DMF, MC and methanol and completely dried. The dried peptidyl resin was added to a round bottom flask and reacted with 30 ml of the leaving solution (TFA 95%, distilled water 2.5% and thioanisole 2.5%) for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 0.98 g of unpurified acetyl-decapeptide (Ac-YRSRKYTSWY-OH) (yield 65.7%).

The unpurified peptides were fractionated using a high performance liquid chromatography, and major peptides were collected and subjected to distillation to remove acetonitrile, followed by lyophilization to give 0.72 g of purified peptides of interest. The finally prepared peptide was analyzed using high performance liquid chromatography to show 96% purity. The final yield was 70.9%. The molecular weight of the final product was measured as 1452.6 (theoretical MW 1451.63) using a molecular weight analyzer, demonstrating that the peptide of interest, Ac-YRSRKYTSWY-OH was successfully synthesized.

Example 11

Synthesis of Formyl-Decapeptide
(Formyl-YRSRKYTSWY-OH)

Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-CTL-resin prepared in Example 2 was swelled using DMF, reacted twice with 20% piperidine/DMF solution for 10 min and washed to remove Fmoc protecting groups. 2 ml of formic acid, 610 mg of HoBt and 1.77 g of Bop were introduced into a new reactor, and then 1.56 ml of DIEA was added to the reactor, followed by agitating. Pre-made acetic acid anhydride was introduced into the reactor containing the resin and the reaction was undertaken for 30 min. The resin was washed three times sequentially with DMF, MC and methanol and completely dried. The dried peptidyl resin was added to a round bottom flask and reacted with 30 ml of the leaving solution (TFA 95%, distilled water 2.5% and thioanisole 2.5%) for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.28 g of unpurified formyl-decapeptide (Formyl-YRSRKYTSWY-OH) (yield 86.6%). The molecular weight of the final product was measured as 1438.1 (theoretical MW 1437.6) using a molecular weight analyzer.

Example 12

Synthesis of Palmitoyl-Decapeptide
(Palmitoyl-YRSRKYTSWY-OH)

Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-CTL-resin prepared in Example 2 was swelled using DMF, reacted twice with 20% piperidine/DMF solution for 10 min and washed to remove Fmoc protecting groups. 1.5 mmol palmitoyl chloride (Sigma-Aldrich) in 5 ml DMF and 1.56 ml of DIPEA were introduced the reactor containing the swelled resin and reaction was carried out for 1 hr at 35° C. The resultant was washed three times with 30 ml DMF and four times with 30 ml DCM and dried under nitrogen atmosphere and then dried using $P_2O_5$ under reduced pressure, yielding decapeptides having side chains protected with palmitoyl groups. 1 g of the dried peptidyl resin was added to a round bottom flask and reacted with 10 ml of the leaving solution (TFA 95%, distilled water 2.5% and thioanisole 2.5%) for 1 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.33 g of unpurified palmitoyl-decapeptide (palmitoyl-YRSRKYTSWY-OH) (yield 73.4%). The molecular weight of the final product was measured as 1664.7 (theoretical MW 1664.01) using a molecular weight analyzer.

Examples 13-14

Synthesis of Myristyl-Decapeptide
(Myristyl-YRSRKYTSWY-OH) and
Stearyl-Decapeptide (Stearyl-YRSRKYTSWY-OH)

Fmoc-Tyr(tBu)-Arg(pbf)-Ser(tBu)-Arg(pbf)-Lys(Boc)-Tyr(tBu)-Thr(tBu)-Ser(tBu)-Trp(Boc)-Tyr(tBu)-CTL-resins prepared in Example 2 were divided into two batches, swelled using DMF, reacted twice with 20% piperidine/DMF solution for 10 min and washed to remove Fmoc protecting groups. 1.5 mmol myristyl chloride (Sigma-Aldrich) in 5 ml DMF (myristyl-decapeptide) for or 1.5 mmol stearyl chloride (Sigma-Aldrich) in 5 ml DMF (stearyl-decapeptide) and 1.56 ml of DIPEA were introduced the reactor containing the resin and reaction was carried out for 1 hr at 35° C. The resultant was washed three times with 30 ml DMF and four times with 30 ml DCM and dried under nitrogen atmosphere and then dried using $P_2O_5$ under reduced pressure, yielding decapeptides having side chains protected with myristyl or stearyl groups. 1 g of the dried peptidyl resin was added to a round bottom flask and reacted with 10 ml of the leaving solution (containing 81.5% TFA, 5% distilled water, 5% thioanisole, 5% phenol, 2.5% EDT and 1% TIS) for 1 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.52 g of unpurified myristyl-decapeptide (myristyl-YRSRKYTSWY-OH) (yield 90.6%) and 1.35 g of unpurified stearyl-decapeptide (stearyl-YRSRKYTSWY-OH) (yield 77.9%). The molecular weights of the final products were measured as 1637.1 (theoretical MW 1635.96) for myristyl-decapeptide and 1692.8 (theoretical MW 1692.07) for stearyl-decapeptide using a mass analyzer.

Example 15

Analysis of Binding Ability of Acetyl-Decapeptide to the Receptor of Basic Fibroblast Growth Factor To examine the binding potency of the purified acetyl-decapepetide of Example 10 to the receptor of basic fibroblast growth factor, the competitive binding assay was carried out using baby hamster kidney cells (BHK, the Korean Cell Line Bank) and $^{125}$I-labeled bFGF (Amersham) according to process proposed by Baird et al. (Baird, et al., *Proc. Natl. Acad. Sci. USA*, 85:2324-2328 (1988)). Cells were cultured in 48-well plates for tissue culture and washed with cold Ham's F12 medium containing 0.2% gelatin (Sigma-Aldrich). 200 fmol of $^{125}$I-bFGF and 1-100 nmol of acetyl decapeptide were dissolved in 200 µl of buffer and incubated with cells for 2 hr. Following the collection of cells by centrifugation, the cell membranes were isolated using 0.1% Triton X-100 and the radioactivity of $^{125}$I-bFGF bound to receptors on cell membrane was determined using a gamma scintillation counter (Packard, U.S.A) (FIG. 3).

Figure 3:
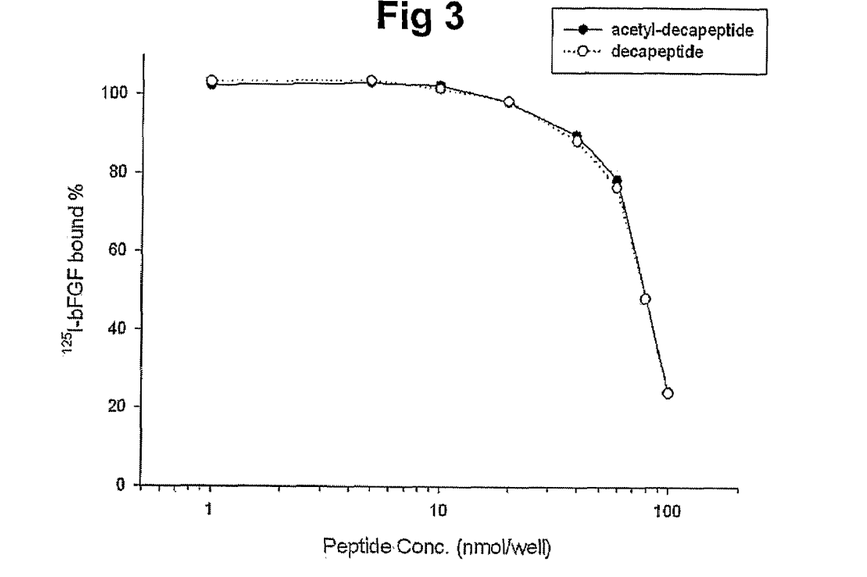
FIG. 3 represents analysis results of the binding potency of the acetyl-decapeptide to the receptor of basic fibroblast growth factor.

As shown in FIG. 3, it was revealed that the acetyl-decapepetide of this invention binds to bFGF receptor in a competitive manner with bFGF. In addition, it was concluded that the acetyl-decapepetide has a higher binding potency to bFGF receptor.

Example 16

Measurement of Biological Activities of Acetyl-Decapeptide

Figure 4:
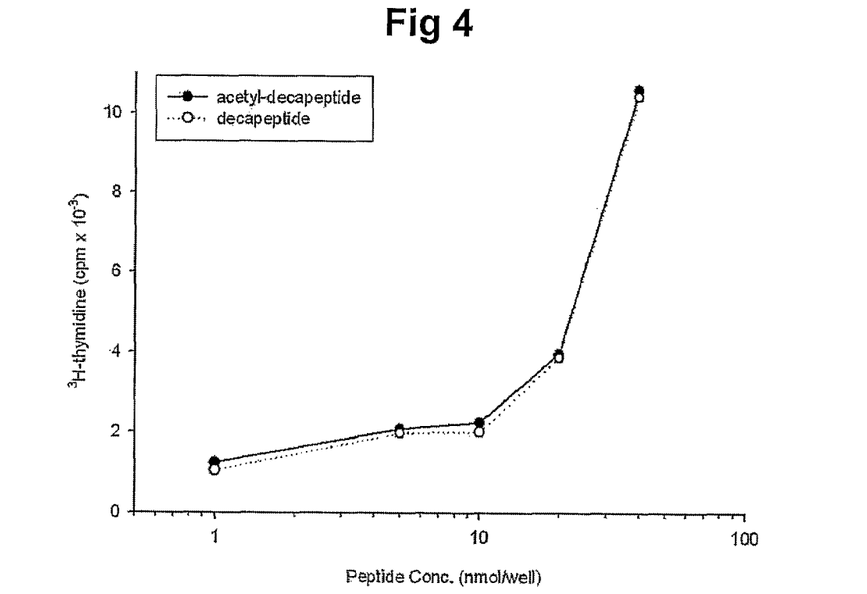
FIG. 4 represents measurement results of biological activities of the acetyl-decapeptide.

The biological activities of the purified acetyl-decapepetide of Example 10 were evaluated using 3T3 fibroblast (The Korean Cell Line Bank) according to Rizzino et al method to measure [$^3$H]-thymidine incorporation (Rizzino, et al. *Cancer Res.*, 48:4266 (1988)). 3T3 cells were cultured in 250 ml-flasks containing EMEM (Eagle's minimal essential media, Gibco, U.S.A.) supplemented with 100% FBS (fetal bovine serum). 3T3 cells cultured were treated with 0.25% trypsin solution to detach cells from the bottom of culture flasks and centrifuged to collect cell pellets. Cells were resuspended in EMEM not containing FBS, its aliquot, $2\times10^4$ cells/0.3 ml medium was added to each well of 24-well plates and cultured under 7% $CO_2$ for 24 hr at 37° C. 2 ng/ml of the acetyl decapeptide of this invention was serially diluted by two-fold using EMEM containing 0.2 (w/v) % bovine serum albumin and 0.3 ml of the diluted peptide was added to each well, followed by additional culturing under 7% $CO_2$ for 6 hr at 37° C. Afterwards, 0.5 µCi of [$^3$H]-thymidine (Amersham, TRK 686, 68 Ci/mmol) was added to each well and incubated overnight. After removing supernatants, cells were washed once using PBS (phosphate buffered saline) and incubated with 0.1 ml of 0.25% trypsin solution for 5 min at 37° C. to detach cells from the bottom of plates. 0.5 ml of EMEM containing 10% FBS was added to each well and cells were adhered to glass fiber filters using a cell harvester (12 well cell harvester, Millipore, U.S.A.). The filters were washed once with 1 ml of distilled water and once with 1 ml of ethanol, and kept to stand for 30 min at 60° C. for drying. The dried filters were added along with 2 ml of scintillation cocktail to scintillation vials and allowed to stand for 30 min at room temperature, after which radioactivity incorporated into cells was determined using a scintillation counter (Beckman, U.S.A).

As represented in FIG. 4, the acetyl decapeptide of this invention promotes thymidine incorporation into fibroblasts in a dose-dependent fashion. Therefore, it could be appreciated that the acetyl decapeptide of this invention has high biological activities similar to intact bFGF.

Example 17

Evaluation of Stability of Acetyl Decapeptide

Figure 5:
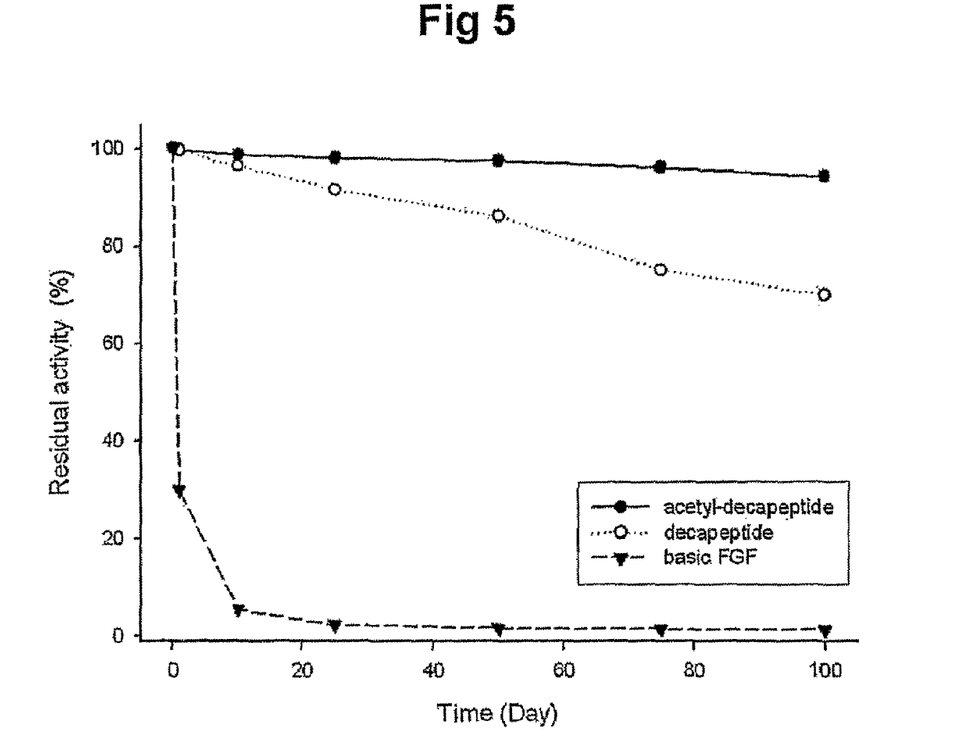
FIG. 5 represents analysis results of stability of the acetyl-decapeptide.

To evaluate stability of the purified acetyl decapeptide of Example 10, the decapeptide and acetyl decapeptide were dissolved in 50 mM Tris-HCl (pH 8.0) to a concentration of 10 µg/ml. A recombinant bFGF produced *E. coli* (Sigma-Aldrich) was prepared as a control in the same buffer to a concentration of 1 µg/ml. The prepared solutions were introduced into glass vials and kept to stand at 37° C. Afterwards, the solutions were taken on days 0, 1, 10, 25, 50, 75 and 100 and subjected to MTT assay (Scudiero, D. A., et al. *Cancer Res.* 48:4827-4833 (1988)) using NIH-3T3 cell (Korean Cell Line Bank) to determine residual activities of peptides and bFGF (FIG. 5). The results were given as relative values to the activity (100%) of sample taken on day 0.

As represented in FIG. 5, the activity of the recombinant bFGF was sharply decreased with the lapse of time. In contrast, the activity of the present decapeptide was shown not to be decreased over time. In particular, the acetyl decapeptide having N-terminal protected with actetyl groups showed excellent stability.

Example 18

Preparation of Nano Peptides 50 mg of the acetyl decapeptide synthesized in Example 10 was dissolved in 500 ml of distilled water. The peptide solution was mixed with 5 g lecithin, 0.3 ml sodium oleate, 50 ml ethanol and a small amount of oils and its volume was adjusted with distilled water to 1 L. The resulting solution was subjected to a microfluidizer under high pressure for emulsification, thereby providing nanosomes having 100-nm size. The nanosomes were prepared to have a final concentration of about 50 ppm and used as ingredients for cosmetics.

Formulation Example 1

Skin Softener

A skin softener containing nanosomes of acetyl decapeptide prepared in Example 18 was formulated according to the following composition.

TABLE 1

| Ingredients | Content (wt %) |
| --- | --- |
| Acetyl-decapeptide | 0.001 |
| 1,3-butylene glycol | 6.0 |
| Glycerine | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 2

Nutrient Cream

A nutrient cream containing nanosomes of acetyl decapeptide prepared in Example 18 was formulated according to the following composition.

TABLE 2

| Ingredients | Content (wt %) |
| --- | --- |
| Acetyl-decapeptide | 0.001 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerine | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid containing nanosomes of acetyl decapeptide prepared in Example 18 was formulated according to the following composition.

TABLE 3

| Ingredients | Content (wt %) |
| --- | --- |
| Acetyl-decapeptide | 0.002 |
| 1,3-butylene glycol | 4.0 |
| Glycerine | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |
| Perfume | Proper amount |
| Distilled water | Residual amount |
| Total | 100 |

Formulation Example 4

Essence

An essence containing nanosomes of acetyl decapeptide prepared in Example 18 was formulated according to the following composition.

TABLE 4

| Ingredients | Content (wt %) |
| --- | --- |
| Acetyl-decapeptide | 0.005 |
| Glycerine | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Formulation Example 5

Mouthwash

A mouthwash containing the acetyl decapeptide prepared in Example was formulated according to the following composition.

TABLE 5

| Ingredients | Content (wt %) |
| --- | --- |
| Acetyl-decapeptide | 0.005 |
| Ethanol | 15 |
| Glycerine | 10 |
| Polyoxyethylene hydrogenated castor oil | 2 |
| Saccharine | 0.15 |

TABLE 5-continued

| Ingredients | Content (wt %) |
| --- | --- |
| Sodium benzoate | 0.05 |
| Perfume | Proper amount |
| Sodium dihydrogen phosphate | 0.1 |
| Coloring agent | Proper amount |
| Distilled water | 72.7 |

Formulation Example 6

Toothpaste

Toothpaste containing the acetyl decapeptide prepared in Example was formulated according to the following composition.

TABLE 6

| Ingredients | Contents (wt %) |
| --- | --- |
| Acetyl-decapeptide | 0.005 |
| Dicalcium phosphate | 45 |
| Silica | 2 |
| Glycerine | 15 |
| Sodium carboxymethyl cellulose | 1 |
| Carageenan | 0.3 |
| Sodium laurylsulfate | 1.5 |
| Saccharine-Na | 0.1 |
| Perfume | 적량 |
| Sodium paraoxybenzoate | 0.01 |
| Distilled water | 35.09 |

Example 19

Analysis of Effects of Peptides on Growth of HaCaT Keratinocytes

Figure 6:
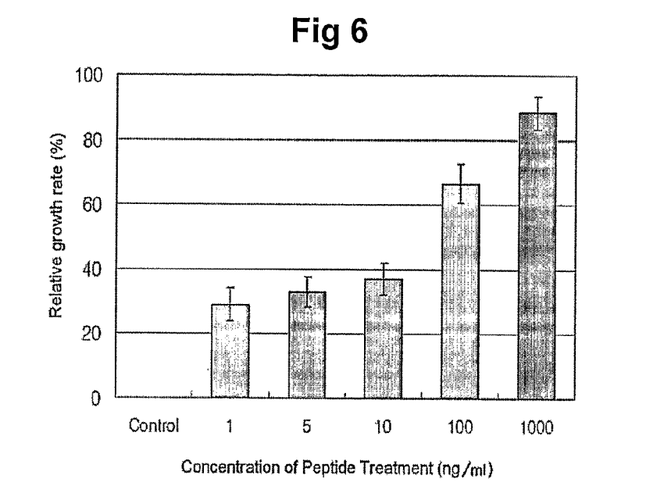
FIG. 6 represents influence of the acetyl-decapeptide on the growth rate of human keratinocytes.
Figure 7:
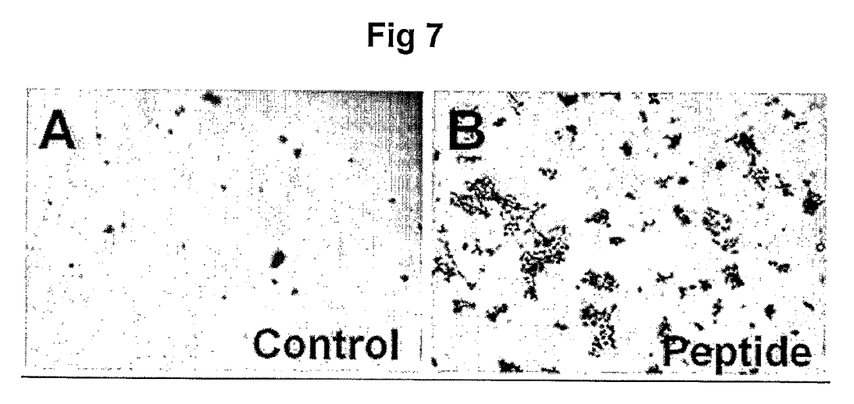
FIG. 7 is a microscope image demonstrating promotion of the acetyl-decapeptide to the growth of human keratinocytes.

To analyze effects of peptides of this invention on proliferation of keratinocytes, SRB (Sulforhodamine B) calorimetric assay was carried out using HaCaT kerationcyte according to Rizzino et al method (Rizzino, et al. *Cancer Res.*, 48:4266 (1988)). HaCaT ketatinocytes (The Korean Cell Line Bank) were cultured in 250 ml-flasks containing EMEM (Eagle's minimal essential media, Gibco, U.S.A.) supplemented with 100% FBS (fetal bovine serum). HaCaT ketatinocytes cultured were treated with 0.25% trypsin solution to detach cells from the bottom of culture flasks and centrifuged to collect cell pellets. Cells were resuspended in EMEM not containing FBS, its aliquot ($4 \times 10^3$) cells was added to each well of 96-well plates and cultured under 7% $CO_2$ for 24 hr at 37° C. After 24-hr culture, the medium was changed with a fresh medium not containing serum and cells were incubated with bFGF or the acetyl-decapeptide of Example 10 (10 ng/ml or 1,000 ng/ml) dissolved in 10% DMSO for 72 hr under the same conditions as described above. After removing supernatants, cells were washed once using PBS (phosphate buffered saline) and incubated with SRB solution (Sigma-Aldrich). Cells were washed with PBS and observed under a microscope to find cell viability. In addition, absorbance at 590 nm was measured to analyze cell proliferation (FIG. 6). FIG. 7 is images of microscope to represent viability of cells treated with peptides for 72 hr.

Figure 8:
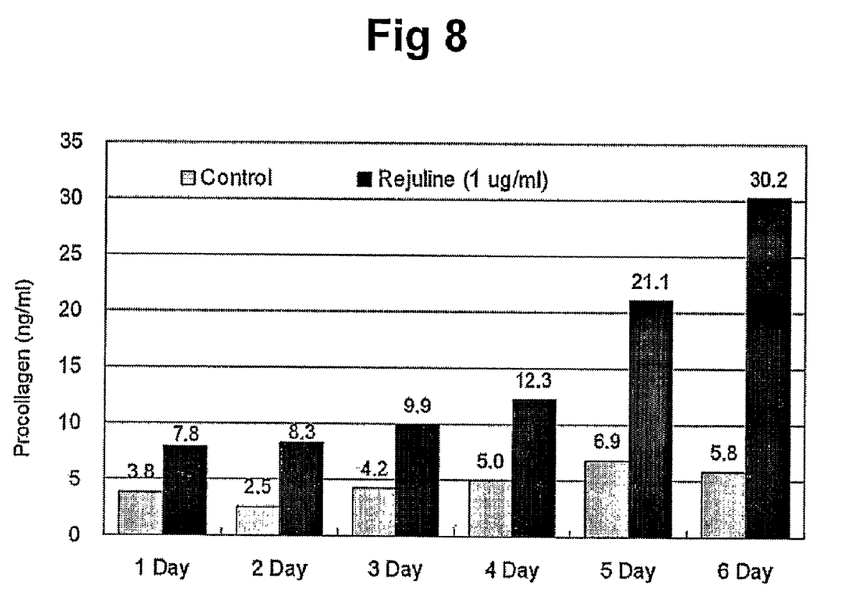
FIG. 8 represents graphs to show the increase in procollagen level where culturing cells with the acetyl-decapeptide.
Figure 9:
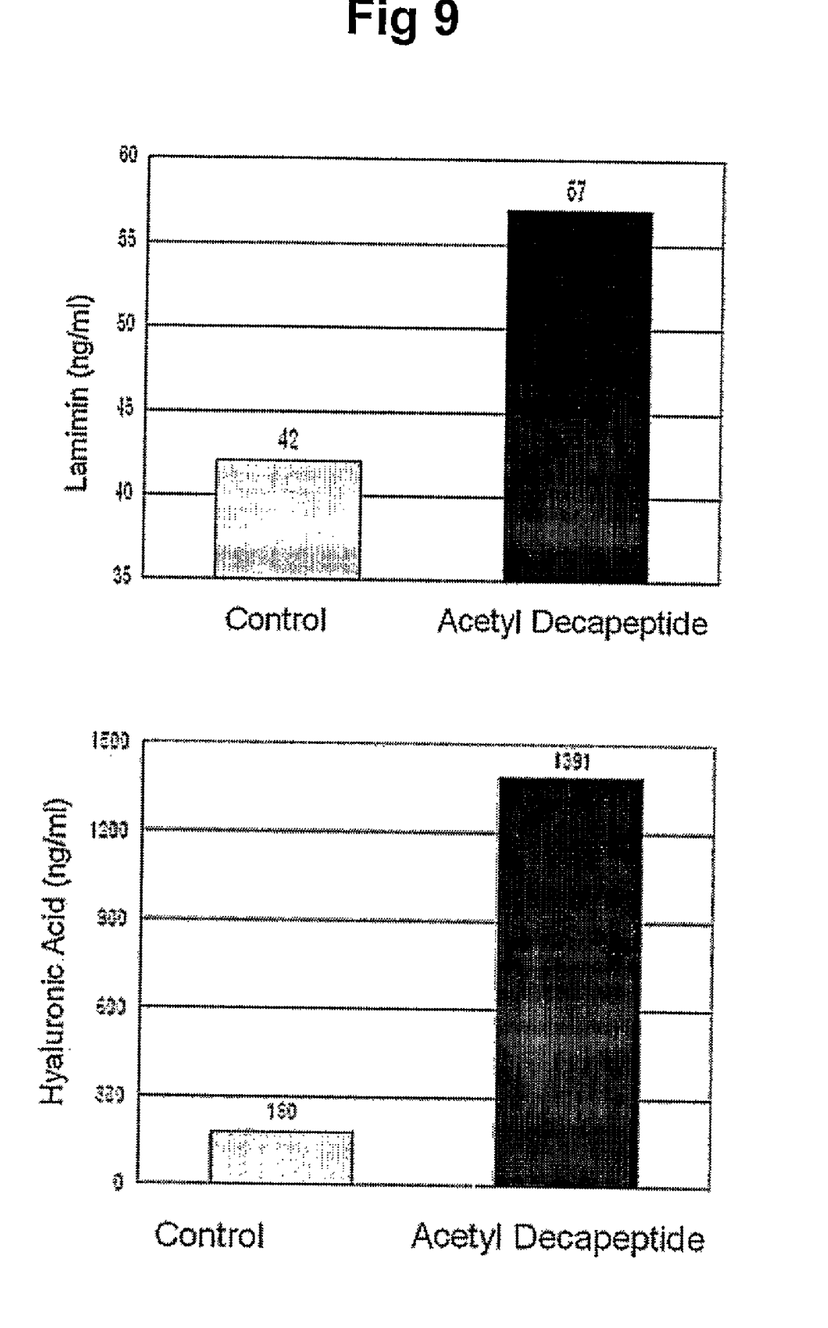
FIG. 9 represents graphs to show the increase in laminin and hyaluronic acid levels where culturing cells with the acetyl-decapeptide.

Furthermore, HaCaT cell line was treated with the acetyl-decapeptide of this invention (1 µg/ml) and the level of procollagen, one of indicators to show the improvement in skin wrinkle, was examined (FIG. 8). The level of procollagen was measured using Procollagen ELISA kit (Takara). For verifying effects on levels of laminin and hyaluronic acid, another indicator representing the improvement in skin wrinkle, HaCaT cell line was incubated with the acetyl-decapeptide of this invention (1 µmole) and levels of laminin and hyaluronic acid were measured using Laminin ELISA kit (CHEMICON, USA) and Hyaluronic acid ELISA kit (Echelon Biosciences Inc, USA), respectively (FIG. 9).

As shown in FIGS. 6 and 7, the peptide of this invention contributed to much higher cell viability than control. Where HaCaT keratinocytes were treated with the present peptide, the level of procollagen in cells was increased in a time-dependent manner (FIG. 8). Moreover, the peptide of this invention was revealed to induce the elevation of levels of laminin and hyaluronic acid (FIG. 9).

Accordingly, these results urge us to reason that the peptides of this invention exhibit significant efficacies to improve skin wrinkle.

Example 20

Analysis of Effects of Peptides on Skin Thickness

For evaluating applicability to cosmetics and in vivo efficacies of the peptides of this invention, the nutrient cream formulated in Formulation Example 2 was applied onto mouse skin.

6-old-week Balb C male mice (Central Lab. Animal, Inc., Korea) were subjected to one-week stabilization and hairs of their back were partially removed using thioglycolic acid-containing cream. Mice were divided into two groups; one group of which was topically administered with the cream comprising acetyl decapeptide-containing nanosomes and the other group of which was topically administered with cream not containing nanosomes. The application of creams was performed every morning (A.M. 8:30) and evening (P.M. 6:30) for 5 days in the dose of 100 mg. After the application, mice were sacrificed by cervical dislocation and their skin tissues were paraffinized. Paraffinized tissues were sectioned using a microtomb in a thickness of 8 µm and were stained with hematoxyline/eosin, followed by observation under an optical microscope (FIG. 10).

Figure 10:
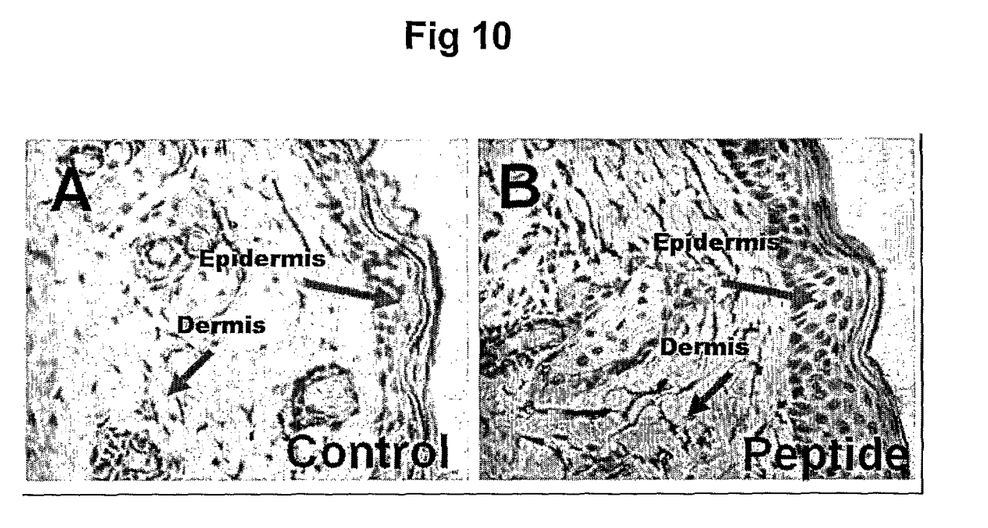
FIG. 10 is a microscope image to show the change in skin thickness of Balb C mice administered with cosmetics containing the acetyl-decapeptide.

As represented in FIG. 10, the nanosome cosmetics comprising the acetyl decapeptide of this invention allowed to promote the formation and growth of keratinocyte layer and epidermal layer. Accordingly, it could be recognized that cosmetics comprising peptides of this invention exert the improvements in skin wrinkle and elasticity.

Example 21

Analysis of Hair-Growth Activities

The hairs of the back portions of Balb C mice were removed and a hair loss-inducing substance, dihydrotestosterone (DHT, TCI Inc.) was applied for 8 days to induce anagen stage before the proliferation of kerationcytes. Afterwards, the Formulation Example 2 was applied onto the back portions once a day for 10 days and then hair growth was observed.

Where the observation was undertaken on day 19 after the hair removal, the normal hair growth was shown in the control subjected only to hair removal. In the group treated with DHT for 8 days and not treated for subsequent 10-days, the hair growth was barely observed. In contrast, where mice subjected to hair removal were treated with DHT for 8 days and subsequently with Formulation Example 2 of this invention, they showed the hair growth over time similar to the control. In this regard, it could be understood that the peptides of this invention posses considerable effects in the promotion of hair growth.

Example 22

Evaluation of Efficacies on Periodontal Disease (Gum Disease)

We examined whether the peptides of this invention have treatment efficacies on periodontal diseases. A mouthwash containing the acetyl decapeptide prepared in Example 10 was formulated according to the following composition: peptide (0.01 wt %), glycerol (12 wt %), sorbitol (10 wt %), propylene glycol (2.8 wt %), SDS-SLS (0.4 wt %), NaF (0.06 wt %) and water (to 100 wt %). Twenty adult subjects were divided into two groups and administered with the peptide-containing mouthwash (Experimental Example) or mouthwash without peptides (Comparative Example). Mouth cleaning with the mouthwash was performed three times a day for 30 days. After 30 days, the sulcus bleeding index that is indicative of periodontal diseases (gum diseases), was determined.

| Items | Comp. Example | | Exp. Example | |
| --- | --- | --- | --- | --- |
| | Day 0 | Day 30 | Day 0 | Day 30 |
| Sulcus bleeding index | 2.01 ± 0.33 | 2.42 ± 0.43 | 1.98 ± 0.62 | 1.25 ± 0.31 |

As indicated in Table, the mouthwash of this invention dramatically reduced the sulcus bleeding index that demonstrates the extent of sulcus bleeding. It was suggested that these efficacies were ascribed to healing of gum wound or scar. Therefore, it could be understood that the mouthwash of this invention improves mouth hygiene of persons having periodontal diseases (gum diseases).

The peptides of this invention exhibit superior efficacies and much better stability and skin permeation than natural-occurring bFGF. In these connections, the composition comprising the peptides of this invention can exhibit excellent efficacies on improvement in skin conditions and treatment of periodontal diseases. In addition, the peptides of this invention can be advantageously applied to pharmaceutical compositions, cosmetics, toothpaste and compositions for mouth cleaning and caring.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for increasing the level of procollagen, laminin or hyaluronic acid in skin tissue; or promoting fibroblast proliferation, keratinocyte layer formation, epidermal layer formation or hair growth, comprising administering to a subject in need thereof a composition comprising a peptide consisting of the amino acid sequence of SEQ ID NO:1 as an active ingredient.

2. The method according to claim 1, wherein the composition is a pharmaceutical composition comprising (a) a pharmaceutically effective amount of the peptide consisting of the amino acid sequence of SEQ ID NO:1; and (b) a pharmaceutically acceptable carrier.

3. The method according to claim 1, wherein the composition is a topical cosmetic composition for use on a skin comprising (a) a cosmetically effective amount of the peptide consisting of the amino acid sequence of SEQ ID NO:1; and (b) a cosmetically acceptable carrier.

4. The method according to claim 1, wherein the amino acid sequence of SEQ ID NO:1 has at least one amino acid residue protected with a protection group selected from the group consisting of acetyl group, fluorenyl methoxy carbonyl group, formyl group, palmitoyl group, myristyl group, stearyl group and polyethylene glycol (PEG).

5. The method according to claim 4, wherein the amino acid residue protected with the protection group is Tyr residue at the N-terminal of the amino acid sequence of SEQ ID NO:1.

6. The method according to claim 1, wherein the peptide has higher stability than naturally occurring basic fibroblast growth factor.

7. The method according to claim 1, wherein the subject has wrinkles, poor skin moisture, poor skin elasticity or insufficient hair.

* * * * *